United States Patent
Lee et al.

(10) Patent No.: US 9,950,309 B2
(45) Date of Patent: Apr. 24, 2018

(54) SUPERABSORBENT POLYMER HAVING HIGH ABSORPTION RATE UNDER LOAD AND PREPARATION METHOD THEREOF

(71) Applicant: LG Chem, Ltd., Seoul (KR)

(72) Inventors: Sang Gi Lee, Daejeon (KR); Soo Jin Lee, Daejeon (KR); Hye Mi Nam, Daejeon (KR); Min Ho Hwang, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/112,081

(22) PCT Filed: Nov. 27, 2015

(86) PCT No.: PCT/KR2015/012861
§ 371 (c)(1),
(2) Date: Jul. 15, 2016

(87) PCT Pub. No.: WO2016/085294
PCT Pub. Date: Jun. 2, 2016

(65) Prior Publication Data
US 2016/0354757 A1  Dec. 8, 2016

(30) Foreign Application Priority Data

Nov. 27, 2014 (KR) .................. 10-2014-0167729
Jan. 21, 2015 (KR) .................. 10-2015-0010157

(51) Int. Cl.
| | | |
|---|---|---|
| B01J 20/282 | (2006.01) | |
| B01J 20/26 | (2006.01) | |
| C08F 20/10 | (2006.01) | |
| C08F 2/10 | (2006.01) | |
| C08J 9/16 | (2006.01) | |
| A61L 15/60 | (2006.01) | |
| B01J 20/30 | (2006.01) | |
| C08J 9/08 | (2006.01) | |
| C08J 9/10 | (2006.01) | |
| C08J 9/224 | (2006.01) | |

(52) U.S. Cl.
CPC ............ *B01J 20/267* (2013.01); *A61L 15/60* (2013.01); *B01J 20/3064* (2013.01); *B01J 20/3085* (2013.01); *C08F 2/10* (2013.01); *C08F 20/10* (2013.01); *C08J 9/08* (2013.01); *C08J 9/10* (2013.01); *C08J 9/106* (2013.01); *C08J 9/16* (2013.01); *C08J 9/224* (2013.01); *C08J 2201/026* (2013.01); *C08J 2203/02* (2013.01); *C08J 2203/04* (2013.01); *C08J 2203/18* (2013.01); *C08J 2205/022* (2013.01); *C08J 2205/048* (2013.01); *C08J 2333/02* (2013.01)

(58) Field of Classification Search
CPC ... B01J 20/267; B01J 20/3064; B01J 20/3085
See application file for complete search history.

(56) References Cited

U.S. PATENT DOCUMENTS

| | | | |
|---|---|---|---|
| 4,394,930 A * | 7/1983 | Korpman ............... | A61F 13/53 215/12.1 |
| 4,446,261 A | 5/1984 | Yamasaki et al. | |
| 5,149,335 A | 9/1992 | Kellenberger et al. | |
| 5,154,713 A | 10/1992 | Lind | |
| 5,314,420 A | 5/1994 | Smith et al. | |
| 5,856,370 A | 1/1999 | Chmelir | |
| 6,261,679 B1 * | 7/2001 | Chen ..................... | A61F 13/53 264/45.2 |
| 6,271,278 B1 * | 8/2001 | Park ...................... | A61L 15/60 521/102 |
| 7,179,851 B2 | 2/2007 | Qin et al. | |
| 2004/0214499 A1 | 10/2004 | Qin et al. | |
| 2004/0214946 A1 * | 10/2004 | Smith ..................... | A61L 15/60 524/556 |
| 2005/0137546 A1 * | 6/2005 | Joy ........................ | A61L 15/60 604/368 |
| 2012/0258851 A1 | 10/2012 | Nakatsuru et al. | |
| 2014/0312273 A1 | 10/2014 | Wattebled et al. | |
| 2015/0093575 A1 | 4/2015 | Naumann et al. | |
| 2015/0197587 A1 | 7/2015 | Lee et al. | |

FOREIGN PATENT DOCUMENTS

| | | |
|---|---|---|
| EP | 0744435 A1 | 11/1996 |
| EP | 0827753 A2 | 3/1998 |
| EP | 2518092 A1 | 10/2012 |
| EP | 2557095 A1 | 2/2013 |
| JP | S56161408 A | 12/1981 |
| JP | S57158209 A | 9/1982 |

(Continued)

OTHER PUBLICATIONS

Buchholz, Fredric L. et al., "Modern Superabsorbent Polymer Technology," 1998, pp. 207-212, WILEY-VCH.
Third Party Observation for Application No. PCT/KR2015/012861, dated Mar. 24, 2017.
Third Party Observation for European Application No. 15862317.3, dated Mar. 28, 2017.
Hwang, Jun Seok et al., Research and Development of Superporous Hydrogels with Fast Swelling and Superabsorbent Properties, Department of Tissue Engineering and Regenerative Medicine, 2008, vol. 5, No. 2, pp. 147-155 (English translation of Conclusion attached).

(Continued)

*Primary Examiner* — Kara B Boyle
(74) *Attorney, Agent, or Firm* — Lerner, David, Littenberg, Krumholz & Mentlik, LLP

(57) ABSTRACT

Provided are a superabsorbent polymer and a preparation method thereof. In the superabsorbent polymer according to the present invention, a low-temperature foaming agent are used together with a high-temperature foaming agent to control the size and distribution of internal pores of the superabsorbent polymer, thereby increasing absorption rate under load without reduction in gel strength.

8 Claims, 3 Drawing Sheets

(56) References Cited

FOREIGN PATENT DOCUMENTS

| | | |
|---|---|---|
| JP | S57198714 A | 12/1982 |
| JP | 2006526691 A | 11/2006 |
| JP | 2014098172 A | 5/2014 |
| KR | 100317398 | 11/2002 |
| KR | 1020060015498 A | 2/2006 |
| KR | 1020060023116 A | 3/2006 |
| KR | 1020140063401 A | 5/2014 |
| KR | 1020140094536 A | 7/2014 |
| KR | 1020140102264 A | 8/2014 |
| WO | 3809801 A1 | 12/1988 |
| WO | 9422502 A1 | 10/1994 |
| WO | 96017884 A1 | 6/1996 |
| WO | 2004096303 A2 | 11/2004 |
| WO | 2004096304 A1 | 11/2004 |
| WO | 2014168858 A1 | 10/2014 |

OTHER PUBLICATIONS

Kabiri, et al., Polym. Int., 52: 1158-1164: Novel approach to highly porous superabsorbent hydrogels: synergistic effect of porogens on porosity and swelling rate.

UV Coatings: Basics, Recent Developments and New Application (Elsevier 2007), p. 115.

Odian, G., Principle of Polymerization (Wiley, 1981), p. 203.

International Search Report for Application No. PCT/KR2015/012861 dated Feb. 29, 2016.

* cited by examiner

[FIG. 1]
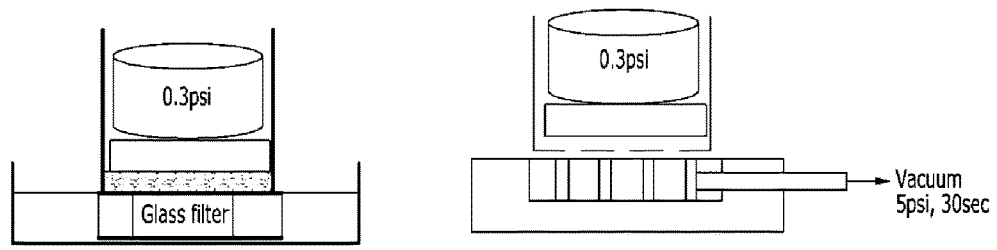
[FIG. 2]
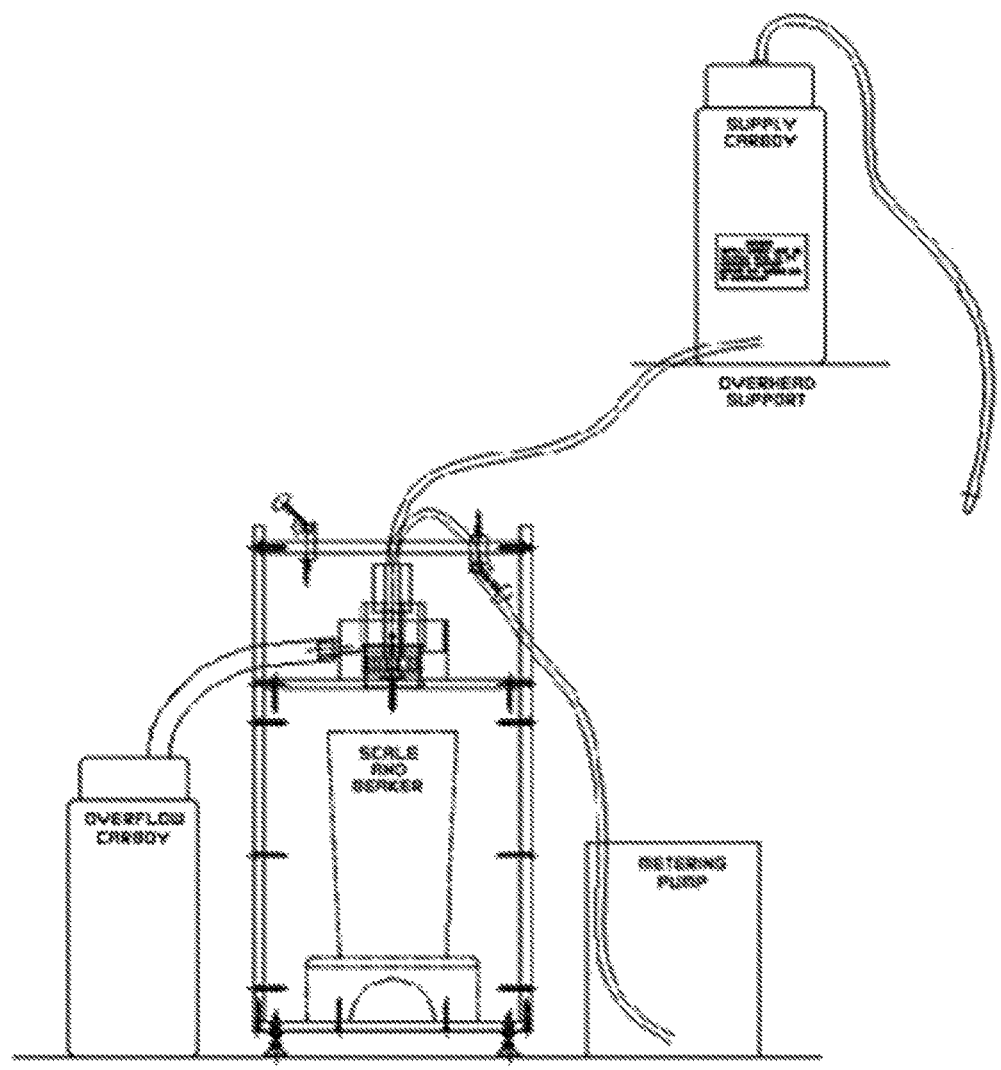

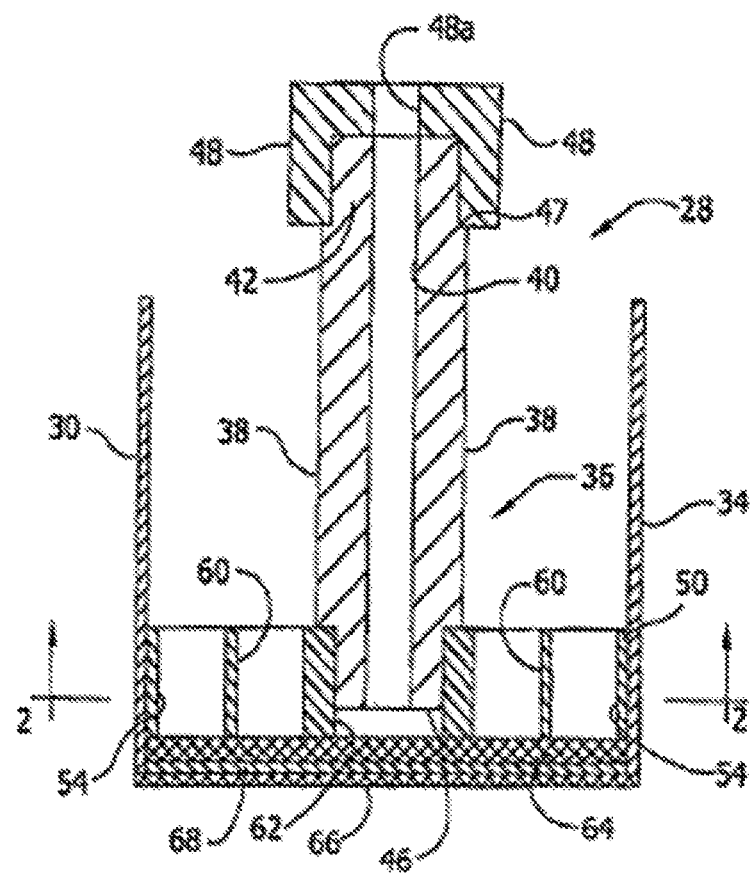
[FIG. 3]

[FIG. 4]
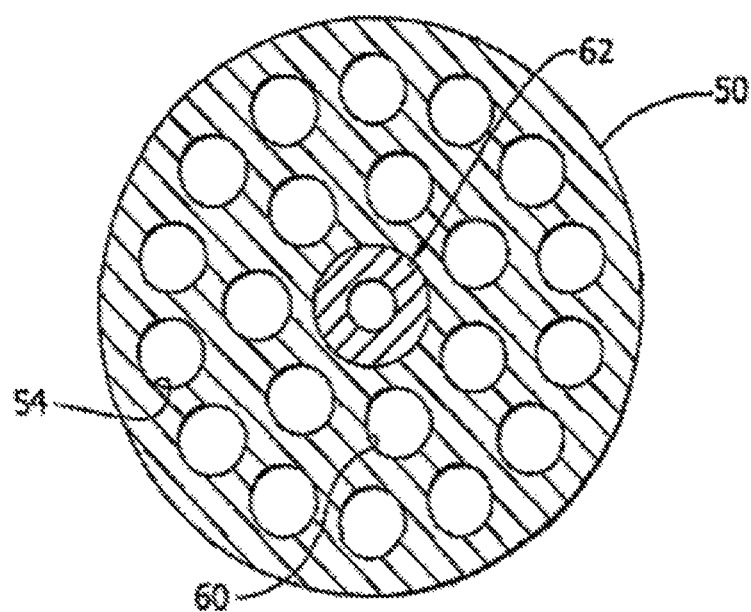

SUPERABSORBENT POLYMER HAVING HIGH ABSORPTION RATE UNDER LOAD AND PREPARATION METHOD THEREOF

CROSS-REFERENCE TO RELATED APPLICATION

The present application is a national phase entry under 35 U.S.C. § 371 of International Application No. PCT/KR2015/012861, filed Nov. 27, 2015, which claims priority from Korean Patent Application No. 10-2014-0167729, filed Nov. 27, 2014, and Korean Patent Application No. 10-2015-0010157 filed, Jan. 21, 2015, the disclosures of which are incorporated herein by reference.

TECHNICAL FIELD

The present invention relates to a superabsorbent polymer having a high absorption rate under load, and a preparation method thereof.

BACKGROUND ART

A superabsorbent polymer (SAP) is a type of synthetic polymeric materials capable of absorbing moisture from about 500 to 1000 times its own weight, and also called SAM (Super Absorbency Material), AGM (Absorbent Gel Material), etc. Since superabsorbent polymers started to be practically applied in sanitary products, now they have been widely used not only for hygiene products such as disposable diapers for children, etc., but also for water retaining soil products for gardening, water stop materials for the civil engineering and construction, sheets for raising seedling, fresh-keeping agents for food distribution fields or the like.

As a preparation process for such superabsorbent polymers, a process by a reverse phase suspension polymerization and a process by a solution polymerization have been known. Of them, preparation of the superabsorbent polymer by reverse phase suspension polymerization is disclosed in, for example, Japanese Patent Laid-open Publication Nos. S56-161408, S57-158209, S57-198714, etc. Further, preparation of the superabsorbent polymer by the solution polymerization further includes a thermal polymerization method in which a water-containing gel polymer is polymerized while being broken and cooled in a kneader equipped with a plurality of shafts, and a photo-polymerization method in which an aqueous solution with a high concentration is irradiated with UV rays onto a belt to be polymerized and dried at the same time.

Meanwhile, absorption rate, one of important physical properties of the superabsorbent polymer, is associated with surface dryness of products in contact with the skin, such as diapers. Generally, absorption rate may be improved by increasing surface area of the superabsorbent polymer.

For example, a method of forming a porous structure on the particle surface of the superabsorbent polymer by using a foaming agent is applied. However, since it is difficult to form a sufficient amount of the porous structure by a general foaming agent, there is a drawback that the absorption rate is not greatly increased.

The method of forming the porous structure on the particle surface by using a foaming agent is as described in a literature (Kabiri, K., Omidian, H. and Zohuriaan-Mehr, M. (2003), Novel approach to highly porous superabsorbent hydrogels: synergistic effect of porogens on porosity and swelling rate. Polym. Int., 52: 1158-1164). As various factors influencing pore formation, the literature suggests gelation time in polymerization as well as selection of a proper porogen, and porogen injection time and method. Carbonate-based materials are suggested as foaming agents generally known, and a time point of injection of these foaming agents is suggested as an important factor of forming the pore structure.

Another example is a method of increasing surface area by re-granulating powder obtained in the preparation process of the superabsorbent polymer to form non-uniform porous particles. This method may be used to improve absorption rate of the superabsorbent polymer, but there is a limitation in that centrifuge retention capacity (CRC) and absorbency under pressure (AUP) of the polymer become relatively low. Like this, there is a trade-off between physical properties of the superabsorbent polymer such as absorption rate, centrifuge retention capacity, absorbency under load, etc. Accordingly, there is an urgent demand for a preparation method capable of improving these physical properties at the same time.

DISCLOSURE

Technical Problem

The present invention is intended to provide a superabsorbent polymer having high gel strength and high absorption rate under load.

Further, the present invention is intended to provide a method of preparing the superabsorbent polymer.

Technical Solution

In order to achieve the above objects, the present invention provides a superabsorbent polymer as follows:

the superabsorbent polymer, comprising a crosslinked polymer resulting from polymerization and internal crosslinking of a monomer composition including acrylic acid-based monomers having acidic groups which are at least partially neutralized, and a surface crosslinking layer formed on the surface of the crosslinked polymer, wherein the superabsorbent polymer has centrifuge retention capacity (CRC) as 29.5 g/g or more, absorbency under load (AUL) as 18 g/g or more, gel bed permeability (GBP) as 60 Darcy or more, and 5-min gel-AUL as 18.0 g/g or more.

In the superabsorbent polymers, centrifuge retention capacity (CRC), absorbency under load (AUL), and gel bed permeability (GBP) are evaluated as important physical properties. In particular, products produced by using the superabsorbent polymers, for example, diapers, become thinner, and thus absorption rate under load is considered as a more important property. To increase absorption rate under load, a method of increasing surface area of the superabsorbent polymer is generally used. To this end, a method of forming a large number of pores inside the superabsorbent polymer to rapidly absorb water or a method of reducing the particle size of the superabsorbent polymer is known. However, there is a limitation in the reduction of the particle size of the superabsorbent polymer, and formation of internal pores decreases gel strength, and therefore, it is difficult to make the products thin.

Accordingly, in the present invention, a low-temperature foaming agent are used together with a high-temperature foaming agent to control the size and distribution of internal pores during the preparation of the superabsorbent polymer, thereby increasing absorption rate under load without reduction in gel strength.

In detail, in the present invention, the low-temperature foaming agent is used to generate pores having a diameter of 100 μm to 400 μm in the superabsorbent polymer, and the high-temperature foaming agent is used to generate pores having a diameter of 5 μm to 100 μm in the superabsorbent polymer. Further, the contents of the low-temperature foaming agent and the high-temperature foaming agent are controlled at a ratio (A:B) of a total pore area ratio (A) of micropores having a diameter of 5 μm to 100 μm and a total pore area ratio (B) of macropores having a diameter of 100 μm to 400 μm. The areas of the pores may be measured by a general method in the art. For example, a micro image (100× magnification) of the surface of the superabsorbent polymer is taken by a scanning electron microscope (SEM), and then the numbers of micropores and macropores present on the surface of a predetermined area (2 cm×2 cm) in SEM image are counted to measure the area ratio of the pores.

As described above, the ratio (A:B) of the total pore area ratio (A) of the pores having a diameter of 5 μm to 100 μm and the total pore area ratio (B) of the pores having a diameter of 100 μm to 400 μm is preferably 3:7 to 9:1. When the micropores having a small diameter and the macropores having a large diameter are distributed within the above ratio in the superabsorbent polymer at the same time, absorption rate under load may be improved while preventing reduction in gel strength. More preferably, the ratio of A:B is 4:6 to 8:2.

In the superabsorbent polymer, parts of the low-temperature foaming agent and high-temperature foaming agent used for formation of the pores may remain and may be included in a crosslinking structure of a final polymer. In detail, the superabsorbent polymer may further include the low-temperature foaming agent and the high-temperature foaming agent which are distributed in the crosslinked polymer in the surface crosslinking layer. Specific kinds of the low-temperature foaming agent and the high-temperature foaming agent will be described in the following description of a preparation method.

In the superabsorbent polymer, the acrylic acid-based monomer is a compound represented by the following Chemical Formula 1:

$$R_1-COOM^1 \qquad \text{[Chemical Formula 1]}$$

wherein, $R_1$ is an alkyl group containing an unsaturated bond and having 2 to 5 carbon atoms, and $M^1$ is a hydrogen atom, a monovalent or divalent metal, an ammonium group, or an organic amine salt.

Preferably, the acrylic acid-based monomer may be one or more selected from the group consisting of acrylic acid, methacrylic acid, and a monovalent metal salt, a divalent metal salt, an ammonium salt, and an organic amine salt thereof.

Here, the acrylic acid-based monomers may have acidic groups which are at least partially neutralized. Preferably, those partially neutralized with an alkali substance such as sodium hydroxide, potassium hydroxide, ammonium hydroxide or the like may be used. In this regard, a degree of neutralization of the acrylic acid-based monomer may be 40 mole % to 95 mole %, or 40 mole % to 80 mole %, or 45 mole % to 75 mole %. The range of the neutralization degree may vary depending on the final physical properties. An excessively high degree of neutralization renders the neutralized monomers precipitated, and thus polymerization may not occur readily, whereas an excessively low degree of neutralization not only deteriorates the absorbency of the polymer but also endows the polymer with hard-to-handle properties, such as of elastic rubber.

Further, the concentration of the acrylic acid-based monomer in the monomer composition may be properly controlled, in consideration of polymerization time and reaction conditions, and the concentration may be preferably 20% by weight to 90% by weight, or 40% by weight to 70% by weight, which is for using the gel effect during the polymerization reaction in a high-concentration aqueous solution to eliminate a need for removing the unreacted monomer after the polymerization and also for improving pulverization efficiency upon a subsequent pulverization process of the polymer. However, if the concentration of the monomer is too low, the yield of the superabsorbent polymer may become low. On the contrary, if the concentration of the monomer is too high, there is a process problem that a part of the monomers is precipitated, or pulverization efficiency is lowered upon pulverization of the polymerized water-containing gel polymer, and the physical properties of the superabsorbent polymer may be reduced.

Meanwhile, the monomer composition may include a crosslinking agent for improving physical properties of the water-containing gel polymer. The crosslinking agent is a first crosslinking agent (internal crosslinking agent) for internal crosslinking of the water-containing gel polymer, and the crosslinking agent is separately used in a subsequent process, independent of a second crosslinking agent (surface crosslinking agent) for surface crosslinking of the water-containing gel polymer.

Preferably, the crosslinked polymer may be internally crosslinked by one or more first crosslinking agents selected from the group consisting of N,N'-methylenebisacrylamide, trimethylolpropane tri(meth)acrylate, ethylene glycol di(meth)acrylate, polyethylene glycol (meth)acrylate, propylene glycol di(meth)acrylate, polypropylene glycol (meth)acrylate, butanediol di(meth)acrylate, butylene glycol di(meth)acrylate, diethylene glycol di(meth)acrylate, hexanediol di(meth)acrylate, triethylene glycol di(meth)acrylate, tripropylene glycol di(meth)acrylate, tetraethylene glycol di(meth)acrylate, dipentaerythritol pentacrylate, glycerin tri(meth)acrylate, pentaerythritol tetraacrylate, triarylamine, ethylene glycol diglycidyl ether, propylene glycol, glycerin, and ethylene carbonate.

Further, the superabsorbent polymer is preferably a particulate polymer having a particle diameter of 150 to 850 μm.

Further, the centrifuge retention capacity (CRC) may be represented by the following Mathematical Equation 1:

$$CRC \ (g/g) = \{[W_2 \ (g) - W_1 \ (g)]/W_0 \ (g)\} - 1 \qquad \text{[Mathematical Equation 1]}$$

wherein, $W_0$ (g) is the weight (g) of the superabsorbent polymer, $W_1$ (g) is the weight (g) of the apparatus, which is measured after draining water off at 250 G for 3 minutes using a centrifuge without the superabsorbent polymer, and $W_2$ (g) is the weight (g) of the apparatus including the superabsorbent polymer, which is measured after immersing the superabsorbent polymer in 0.9 wt % physiological saline solution at room temperature for 30 minutes and draining water off at 250 G for 3 minutes using a centrifuge.

Further, the absorbency under load (AUL) may be represented by the following Mathematical Equation 2:

$$AUL \ (g/g) = [W_4 \ (g) - W_3 \ (g)]/W_0 \ (g) \qquad \text{[Mathematical Equation 2]}$$

wherein, $W_0$ (g) is the weight (g) of the superabsorbent polymer, $W_3$ (g) is the sum (g) of the weight of the superabsorbent polymer and the weight of the apparatus capable of providing a load for the superabsorbent polymer, and $W_4$ (g) is the sum (g) of the weight of the water-absorbed superabsorbent polymer after supplying water for the superabsorbent polymer under a load (0.9 psi) for 60 minutes and the weight of the apparatus capable of providing a load for the superabsorbent polymer.

Further, the 5-min gel-AUL may be represented by the following Mathematical Equation 2-1:

$$\text{5-min gel-AUL (g/g)} = [W_4 \text{ (g)} - W_3 \text{ (g)}]/W_0 \text{ (g)} \qquad \text{[Mathematical Equation 2-1]}$$

wherein, $W_0$ (g) is the weight (g) of the superabsorbent polymer, $W_3$ (g) is the sum (g) of the weight of the superabsorbent polymer and the weight of the apparatus capable of providing a load for the superabsorbent polymer, and $W_4$ (g) is the sum (g) of the weight of the water-absorbed superabsorbent polymer after supplying water for the superabsorbent polymer under a load (0.3 psi) for 5 minutes and the weight of the apparatus capable of providing a load for the superabsorbent polymer.

Further, the superabsorbent polymer according to the present invention may be prepared by a preparation method comprising the following steps of:

1) polymerizing or crosslinking a monomer composition including acrylic acid-based monomers having acidic groups which are at least partially neutralized, in the presence of a polymerization initiator, a first crosslinking agent, a low-temperature foaming agent, and a high-temperature foaming agent at 25 to 100° C. to form a water-containing gel polymer, 2) coarsely pulverizing the water-containing gel polymer, 3) drying the coarsely pulverized water-containing gel polymer at 150 to 250° C., 4) pulverizing the dried polymer, and 5) surface-modifying the pulverized polymer by a second crosslinking agent.

Hereinafter, each step of the present invention will be described in detail.

Step of Forming the Water-Containing Gel Polymer (Step 1)

The acrylic acid-based monomers having acidic groups which are at least partially neutralized are the same as described above, and Step 1 is a step of polymerizing the acrylic acid-based monomers to prepare the water-containing gel polymer.

Specifically, in the present invention, the monomer composition is characterized by including the low-temperature foaming agent and the high-temperature foaming agent, in addition to the polymerization initiator and the first crosslinking agent. The low-temperature foaming agent means a foaming agent which generates pores at 60° C. or lower. Since the polymerization and crosslinking of Step 1 are performed at a temperature of 25 to 100° C., foaming by the low-temperature foaming agent occurs during Step 1. In this regard, the prepared water-containing gel polymer includes water to have low viscosity, and thus pores generated by foaming are larger than those generated by the high-temperature foaming agent described below.

As the low-temperature foaming agent, sodium bicarbonate, sodium carbonate, potassium bicarbonate, potassium carbonate, calcium bicarbonate, calcium carbonate, magnesium bicarbonate, or magnesium carbonate may be used.

Further, the polymerization and crosslinking are preferably performed at a temperature of 30 to 90° C.

As the high-temperature foaming agent, an organic foaming agent capable of generating air bubbles by decomposition at a high temperature may be used, and exemplified by azodicarbonamide (ADCA), dinitroso pentamethylene tetramine (DPT), p,p'-oxybisbenzenesulfonylhydrazide (OBSH), p-toluenesulfonyl hydrazide (TSH), and sugar ester. The sugar ester includes sucrose stearate, sucrose palmitate, sucrose laurate, etc., and represented by S-970, S-1570, S-1670, P-1670 and LAW-1570. The decomposition temperature of the high-temperature foaming agent is higher than about 100° C., and preferably 120 to 180° C., and therefore, the high-temperature foaming agent is rather decomposed to generate macropores during the drying process of Step 3 than decomposed to generate micropores during the polymerization and crosslinking reactions of Step 1.

Further, a ratio (A:B) of a total pore area ratio (A) of micropores having a diameter of 5 μm to 100 μm and a total pore area ratio (B) of macropores having a diameter of 100 μm to 400 μm in the superabsorbent polymer may be controlled by controlling a weight ratio of the low-temperature foaming agent and the high-temperature foaming agent, and preferably, the weight ratio of the low-temperature foaming agent and the high-temperature foaming agent is 50:1 to 2:1.

The polymerization initiator may be any polymerization initiator generally used in the preparation of the superabsorbent polymer. As the polymerization initiator, a thermal polymerization initiator or a photo-polymerization initiator may be used depending on a polymerization method. However, even though the photo-polymerization is performed, a certain amount of heat is generated by UV irradiation or the like and is also generated with exothermic polymerization reaction. Therefore, the thermal polymerization initiator may be further included even though photo-polymerization is performed.

The photo-polymerization initiator may be, for example, one or more compounds selected from the group consisting of benzoin ether, dialkyl acetophenone, hydroxyl alkylketone, phenyl glyoxylate, benzyl dimethyl ketal, acyl phosphine, and α-aminoketone. As the specific example of acyl phosphine, commercial Lucirin® TPO, namely, 2,4,6-trimethyl-benzoyl-trimethyl phosphine oxide, may be used. More various photo-polymerization initiators are well disclosed in "UV Coatings: Basics, Recent Developments and New Applications" written by Reinhold Schwalm, (Elsevier, 2007), p 115, which may be served as a reference.

Further, the thermal polymerization initiator may be one or more compounds selected from the group consisting of persulfate-based initiators, azo-based initiators, hydrogen peroxide, and ascorbic acid. Specific examples of the persulfate-based initiators may include sodium persulfate ($Na_2S_2O_8$), potassium persulfate ($K_2S_2O_8$), ammonium persulfate (($NH_4$)$_2S_2O_8$) or the like. Further, specific examples of the azo-based initiators may include 2,2-azobis(2-amidinopropane) dihydrochloride, 2,2-azobis-(N,N-dimethylene) isobutyramidine dihydrochloride, 2-(carbamoylazo)isobutylonitril, 2,2-azobis(2-[2-imidazolin-2-yl]propane) dihydrochloride, 4,4-azobis-(4-cyanovaleric acid) or the like. More various thermal polymerization initiators are well-disclosed in "Principle of Polymerization" written by Odian, (Wiley, 1981), p 203, which may be served as a reference.

The polymerization initiator may be added at a concentration of about 0.001% by weight to 1% by weight, based on the monomer composition. That is, if the concentration of the polymerization initiator is too low, the polymerization rate becomes low and thus a large amount of residual monomers may be undesirably extracted from the final product. On the contrary, if the concentration of the polymerization initiator is too high, the polymer chains constituting the network becomes short, and thus the content of water-soluble components is increased and physical properties of the polymer may deteriorate such as a reduction in absorbency under load.

The first crosslinking agent is the same as defined above, and is a first crosslinking agent (internal crosslinking agent) for internal crosslinking of the water-containing gel polymer, and separately used in a subsequent process, independent of the second crosslinking agent (surface crosslinking agent) for surface crosslinking of the water-containing gel polymer. The first crosslinking agent may be added in an amount of about 0.001% by weight to 1% by weight, based on the monomer composition. If the concentration of the first crosslinking agent is too low, the polymer may have low absorption rate and low gel strength, undesirably. On the contrary, if the concentration of the first crosslinking agent is too high, the polymer may have low absorption ability, which is not preferred as an absorbent.

In addition, the monomer composition may further include an additive such as a thickener, a plasticizer, a preservation stabilizer, an antioxidant, etc., if necessary.

Further, the raw materials such as the above-described acrylic acid-based monomers, polymerization initiator, first crosslinking agent, low-temperature foaming agent, and high-temperature foaming agent may be prepared in the form of a solution of the monomer composition which is dissolved in a solvent. In this regard, as the solvent, any solvent may be used without limitations in the constitution, as long as it is able to dissolve the above ingredients. For example, one or more selected from water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, N,N-dimethylacetamide, or a mixture thereof may be used as the solvent. The amount of the solvent may be controlled at a weight ratio of 1 to 5 times with respect to the content of the acrylic acid-based monomer, in consideration of the polymerization heat control. Further, when the low-temperature foaming agent and the high-temperature foaming agent are mixed with water or dissolved in acrylic acid, no additional solvent may be used.

On the other hand, formation of the water-containing gel polymer by polymerizing and crosslinking the monomer composition may be performed by a general method known in the art to which the present invention pertains, and the process is not particularly limited. A non-limiting example of the polymerization method is largely classified into the thermal polymerization and the photo-polymerization according to the polymerization energy source, and the thermal polymerization may be carried out in a reactor like a kneader equipped with agitating spindles and the photo-polymerization may be carried out in a reactor equipped with a movable conveyor belt.

For example, the monomer composition is injected to a reactor like a kneader equipped with the agitating spindles, and thermal polymerization is performed by providing hot air thereto or heating the reactor so as to obtain the water-containing gel polymer. In this regard, the water-containing gel polymer may have the size of centimeters or millimeters when it is discharged from the outlet of the reactor, according to the type of agitating spindles equipped in the reactor. The water-containing gel polymer may be obtained in various forms according to the concentration of the monomer composition fed thereto, the feeding speed or the like, and the water-containing gel polymer having a weight average particle diameter of 2 to 50 mm may be generally obtained.

Further, when the photo-polymerization of the monomer composition is carried out in a reactor equipped with a movable conveyor belt, the water-containing gel polymer may be obtained in a sheet-type. In this regard, the thickness of the sheet may vary according to the concentration of the monomer composition fed thereto and the feeding speed, and the polymer sheet is preferably controlled to have a thickness of 0.5 to 5 cm in order to uniformly polymerize the entire sheet and secure production speed.

The water-containing gel polymer formed by the above method may have a water content of about 40% by weight to 80% by weight. In terms of optimization of the efficiency of the drying step described below, it is preferable that the water-containing gel polymer is controlled to have the water content within the above range. The "water content", as used herein, means a water content in the total weight of the water-containing gel polymer, which is obtained by subtracting the weight of the dry polymer from the weight of the water-containing gel polymer. Specifically, the water content is defined as a value calculated by measuring the weight loss according to evaporation of water in the polymer during the drying process of increasing the temperature of the polymer with infrared heating. In this regard, the drying conditions are determined as follows; the temperature is increased from room temperature to about 180° C. and then the temperature is maintained at 180° C., and the total drying time is determined as 40 minutes, including 5 minutes for the temperature rising step.

Step of Coarsely Pulverizing the Water-Containing Gel Polymer (Step 2)

The water-containing gel polymer obtained by the above described step is subjected to a drying process in order to provide the water-containing gel polymer with absorbency. In order to increase efficiency of the drying process, the water-containing gel polymer is subjected to the step of (coarsely) pulverizing the water-containing gel polymer, before the drying process.

A non-limiting example of a pulverizing device applicable to the coarse pulverization may include a vertical pulverizer, a turbo cutter, a turbo grinder, a rotary cutter mill, a cutter mill, a disc mill, a shred crusher, a crusher, a chopper, a disc cutter, etc.

In this regard, the coarse pulverization may be performed so that the water-containing gel polymer has a particle size of about 2 mm to about 10 mm. That is, to increase the drying efficiency, the water-containing gel polymer is preferably pulverized to have a particle size of 10 mm or less. However, excessive pulverization may cause agglomeration between particles, and therefore, the water-containing gel polymer is preferably pulverized to have a particle size of 2 mm or more.

In the coarse pulverization, the polymer may stick to the surface of the pulverizing device because it has high water content. In order to minimize this phenomenon, steam, water, a surfactant, an anti-agglomeration agent (e.g., clay or silica, etc.); a thermal polymerization initiator such as a persulfate-based initiator, an azo-based initiator, hydrogen peroxide; or a crosslinking agent such as an epoxy-based crosslinking agent a diol-based crosslinking agent, a crosslinking agent including 2-functional or 3 or more-functional acrylate, a mono-functional crosslinking agent including a hydroxyl group may be added during the coarse pulverization step.

Step of Drying the Coarsely Pulverized Water-Containing Gel Polymer (Step 3)

The water-containing gel polymer coarsely pulverized by the above described step is subjected to a drying process. The water-containing gel polymer which is coarsely pulverized at a particle size of 2 mm to 10 mm by the above described step is provided for the drying step, thereby further increasing the efficiency of the drying step.

The drying of the coarsely pulverized water-containing gel polymer may be performed at a temperature of 120° C. to 250° C., preferably 140° C. to 200° C., and more preferably 150° C. to 190° C. In this regard, the drying temperature means the temperature of the heating medium provided thereto for drying, or the temperature of the drying reactor including the heating medium and the polymer during the drying process. If the drying temperature is low, and therefore the drying time becomes long, the process efficiency may be decreased. In order to prevent this problem, the drying temperature is preferably 120° C. or higher. In addition, when the drying temperature is higher than necessary, only the surface of the water-containing gel polymer is excessively dried, and thus there is a concern about generation of fine powder during the subsequent pulverization process and deterioration of the physical properties of the polymer finally formed. In order to prevent this problem, therefore, the drying temperature is preferably 250° C. or lower.

As described in Step 1, in the present invention, the high-temperature foaming agent may be used to prepare the water-containing gel polymer, and therefore, the high-temperature foaming agent is included in the coarsely pulverized water-containing gel polymer. The high-temperature foaming agent means a foaming agent which generates pores at 100° C. or higher. Since the drying temperature of Step 3 is higher than 100° C., foaming by the high-temperature foaming agent occurs during Step 3. In this regard, since the coarsely pulverized water-containing gel polymer has low water content during the drying process and thus has high viscosity, pores generated by foaming are smaller than those generated by the low-temperature foaming agent described above.

In this regard, the drying time in the drying step is not particularly limited, but may be controlled to 20 to 90 minutes at the above drying temperature, in consideration of the process efficiency and physical properties of the polymer.

The drying may be carried out by using a general medium, and for example, the coarsely pulverized water-containing gel polymer may be supplied with hot air, or irradiated with infrared rays, microwaves, ultraviolet rays or the like.

When the drying step as above is finished, the water content of the polymer may be preferably about 0.1% by weight to about 10% by weight. In other words, if the water content of the dried polymer is less than 0.1% by weight, production costs may be increased due to excessive drying and degradation of the crosslinked polymer may occur, undesirably. If the water content of the dried polymer is more than 10% by weight, defective products may be undesirably produced in the subsequent process.

Step of Pulverizing the Dried Polymer (Step 4)

The step of pulverizing the polymer which is dried by the above-described step is performed. The pulverization step is a step of optimizing the surface area of the dried polymer, and the step is performed to make the pulverized polymer have a particle diameter of 150 to 850 μm.

In this regard, a pulverization device may include a pin mill, a hammer mill, a screw mill, a roll mill, a disc mill, a jog mill or the like, generally used. Further, a step of selectively size-sorting the polymer particles obtained through the process into the polymer having a particle diameter of 150 to 850 μm may be further performed in order to manage physical properties of the superabsorbent polymer finally produced.

Step of Surface-Modifying the Pulverized Polymer (Step 5)

The step of surface-modifying the polymer which is pulverized by the above-described step is performed in the presence of the second crosslinking agent.

The surface modification is a step of further improving physical properties of the superabsorbent polymer by inducing surface-crosslinking of the surface of the pulverized polymer in the presence of the second crosslinking agent (surface crosslinking agent). A surface crosslinking layer may be formed on the surface of the pulverized polymer particles by the surface-modification.

The surface modification may be performed by a general method of increasing crosslinking density of the surface of the polymer particle, and for example, a solution including the second crosslinking agent (surface crosslinking agent) is mixed with the pulverized polymer to allow crosslinking reaction.

Herein, as long as the second crosslinking agent is a compound that may be with the functional group of the polymer, it may be used without limitation in the constitution thereof. Non-limiting examples of the second crosslinking agent may include one or more compounds selected from the group consisting of ethylene glycol diglycidyl ether, polyethylene glycol diglycidyl ether, glycerol polyglycidyl ether, propylene glycol diglycidyl ether, polypropylene glycol diglycidyl ether, ethylene glycol, diethylene glycol, propylene glycol, triethylene glycol, tetraethylene glycol, propane diol, dipropylene glycol, polypropylene glycol, glycerin, polyglycerin, butanediol, heptanediol, hexanediol, trimethylol propane, pentaerythritol, sorbitol, calcium hydroxide, magnesium hydroxide, aluminum hydroxide, iron hydroxide, calcium chloride, magnesium chloride, aluminum chloride, and iron chloride.

In this regard, the content of the second crosslinking agent may be properly controlled according to the type of the crosslinking agent or reaction conditions, and the content is preferably 0.001 to 5 parts by weight, based on 100 parts by weight of the pulverized polymer. If the content of the second crosslinking agent is too low, surface modification may hardly occur to deteriorate physical properties of the final polymer. On the contrary, if the second crosslinking agent is excessively used, excessive surface crosslinking reaction may occur, leading to deterioration in absorption ability of the polymer.

Meanwhile, the surface modification step may be performed by a method of feeding the second crosslinking agent and the pulverized polymer to the reactor and mixing them, a method of spraying the second crosslinking agent to the pulverized polymer, or a method of mixing the pulverized polymer and the second crosslinking agent while continuously feeding them to a mixer being continuously operated.

The second crosslinking agent may be added with water. When the second crosslinking agent is added together with water, the second crosslinking agent may be evenly dispersed, agglomeration of the polymer particles may be prevented, and the penetrating depth of the second crosslinking agent into the polymer particles may be optimized. Considering these purposes and effects, the amount of water added with the second crosslinking agent may be 0.5 to 10 parts by weight, based on 100 parts by weight of the pulverized polymer.

The surface modification step may be performed at a temperature of 100° C. to 250° C. Further, the surface modification may be performed for 1 to 120 minutes, preferably 1 to 100 minutes, and more preferably 10 to 60 minutes. That is, in order to induce the minimal surface crosslinking reaction and to prevent a reduction in physical properties due to deterioration in the polymer particles during excessive reaction, the surface modification step may be performed under the above described conditions.

Effect of the Invention

The superabsorbent polymer according to the present invention may have improved absorption rate under load without reduction in gel strength by controlling the size and distribution of the internal pores in the superabsorbent polymer in the presence of a low-temperature foaming agent and a high-temperature foaming agent.

BRIEF DESCRIPTION OF DRAWINGS

FIG. 1 illustrates an example of an apparatus for measuring absorption rate under load of a superabsorbent polymer according to an embodiment of the present invention;

FIG. 2 illustrates an example of an apparatus for measuring gel bed permeability (GBP) according to an embodiment of the present invention; and FIGS. 3 and 4 illustrate an example of a cylinder and a mesh arrangement for measuring gel bed permeability.

DETAILED DESCRIPTION OF THE EMBODIMENTS

Hereinafter, the preferred examples are provided for better understanding. However, these examples are for illustrative purposes only, and the present invention is not intended to be limited by these examples.

Example 1

To a 2 L-glass reactor surrounded by a jacket through which a heating medium pre-cooled at 25° C. was circulated, 11 g (110 ppm with respect to a monomer composition) of 0.5% IRGACURE 819 initiator diluted with 500 g of acrylic acid was injected, a solution (solution A) of 26 g of 5% polyethylene glycol diacrylate (PEGDA, molecular weight of 400) diluted with acrylic acid was injected, and a solution (solution B) of 14 g of trimethylolpropane triacrylate (Ethoxylated-TMPTA, TMP(EO)9TA, M-3190 Miwon Specialty Chemical Co., Ltd.) containing 9% mole of 5% ethylene oxide diluted with acrylic acid was injected, 2.8 g of 0.5% S-1570 solution diluted with acrylic acid was added thereto, and then 800 g (solution C) of 24% caustic soda solution was slowly added dropwise. As a water-soluble ethylene-based unsaturated monomer thus obtained, acrylic acid had degree of neutralization of 70 mole % in sodium acrylate.

After confirming that the temperature of the mixture increased to 72° C. or higher by neutralization heat generated upon mixing the two solutions, the mixture was left until reaction temperature reached 40° C. When reaction temperature reached 40° C., 2 g of sodium bicarbonate in a solid phase was mixed with monomers, and 54 g of 2% sodium persulfate solution diluted with water was injected at the same time.

The solution was poured in a Vat-type tray (15 cm in width×15 cm in length) installed in a square polymerizer which had a light irradiation device installed at the top and was preheated to 80° C., and photoinitiation was performed by light irradiation. At about 25 seconds after light irradiation, gel was generated from the surface, and at 50 seconds, bubble formation and polymerization occurred at the same time. Then, the reaction was allowed for additional 3 minutes, and the polymerized sheet was taken and cut in a size of 3 cm×3 cm and then subjected to a chopping process using a meat chopper to prepare crumbs.

The crumbs were dried in an oven capable of shifting airflow up and down. The crumbs were uniformly dried by flowing hot air at 180° C. from the bottom to the top for 15 minutes and from the top to the bottom for 15 minutes. After drying, the dried product had a water content of 2% or less.

After drying, the product was pulverized using a pulverizer and sorted by size, and a size of about 150 to about 850 μm was selected to prepare a base polymer. The base polymer thus prepared had a centrifuge retention capacity of 36.5 g/g and a water-soluble component content of 12.5% by weight.

Thereafter, 100 g of the base polymer was mixed with a crosslinking solution containing 3 g of water, 3 g of methanol, 0.4 g of ethylene carbonate, and 0.2 g of aerosol 200, and surface crosslinking reaction was allowed at 190° C. for 30 minutes. After pulverization, a surface-treated superabsorbent polymer having a particle size of 150 μm to 850 μm was obtained by using a sieve.

Example 2

A superabsorbent polymer was prepared in the same manner as in Example 1, except that sodium bicarbonate was added when temperature of the mixed solution reached 45° C. in Example 1.

Example 3

A superabsorbent polymer was prepared in the same manner as in Example 1, except that 520 g of acrylic acid and 760 g of 24.5% caustic soda solution were used in Example 1. In this case, a sheet was very tough after polymerization, unlike Example 1, and pores on the sheet had smaller size when they were observed with the naked eye.

Example 4

A superabsorbent polymer was prepared in the same manner as in Example 1, except that 3 g of 5% TSH solution diluted with acrylic acid was used instead of S-1570 in Example 1.

Comparative Example 1

A superabsorbent polymer was prepared in the same manner as in Example 1, except that no sodium bicarbonate was used in Example 1.

Comparative Example 2

A superabsorbent polymer was prepared in the same manner as in Example 1, except that no S-1570 was used in Example 1.

Experimental Example

Physical properties of the polymers prepared in Examples 1 to 4 and Comparative Examples 1 to 2 were evaluated as follows.

(1) Particle Size

The particle size of each polymer was measured according to EDANA WSP 220.2 (European Disposables and Nonwovens Association, EDANA).

(2) Centrifuge Retention Capacity (CRC)

Centrifuge retention capacity by absorbency under no load was measured for each polymer according to EDANA WSP 241.2.

In detail, each polymer $W_0$ (g) (about 2.0 g) obtained in Examples and Comparative Examples was uniformly placed into a nonwoven-fabric-made bag, followed by sealing. Then, the bag was immersed in a physiological saline solution (0.9% by weight) at room temperature. After 30 minutes, the bag was drained at 250 G for 3 minutes with a centrifuge, and the weight $W_2$ (g) of the bag was then measured. Further, the same procedure was carried out using no polymer, and the resultant weight $W_1$ (g) was measured. Thus, CRC (g/g) was calculated from the obtained weights according to the following Equation:

$$CRC\ (g/g) = \{[W_2\ (g) - W_1\ (g)]/W_0\ (g)\} - 1 \quad \text{[Mathematical Equation 1]}$$

(3) Absorbency Under Load and Absorption Rate Under Load

—Absorbency Under Load (AUL)

Absorbency under load (AUL) at 0.9 psi was measured for each polymer according to EDANA WSP 242.3, and a device for measuring absorbency under load (AUL) as shown in FIG. 1 was used.

In detail, a 400 mesh stainless steel net was installed in the bottom of the plastic cylinder having the internal diameter of 25 mm. Each of the superabsorbent polymers $W_0$ (g) (0.16 g) obtained was uniformly scattered on the steel net at room temperature and the humidity of 50%, and a piston which may provide a load of 5.1 kPa (0.9 psi) uniformly was put thereon, in which the external diameter of the piston was slightly smaller than 25 mm, there was no gab between the internal wall of the cylinder and the piston, and the jig-jog of the cylinder was not interrupted. At this time, the weight $W_3$ (g) of the device was measured.

After putting a glass filter having a diameter of 90 mm and a thickness of 5 mm in a petri dish having a diameter of 150 mm, a physiological saline solution composed of 0.9% by weight of sodium chloride was poured in the dish until the surface level became equal to the upper surface of the glass filter. A sheet of filter paper having a diameter of 90 mm was put thereon. The measuring device was put on the filter paper and the solution was absorbed for 1 hour under the load. After 1 hr, the weight $W_4$ (g) was measured after lifting the measuring device up.

The weights thus obtained were used to calculate absorbency under load (g/g) according to the following Equation:

$$AUL\ (g/g) = [W_4\ (g) - W_3\ (g)]/W_0\ (g) \quad \text{[Mathematical Equation 2]}$$

—Absorption Rate Under Load

The same method as in the measurement of absorbency under load was performed, except that a load of 0.3 psi was used instead of the load of 0.9 psi, and the polymer was allowed to absorb a physiological saline solution composed of 0.9% by weight of sodium chloride for 5 minutes, and placed on a vacuum pressure plate. The saline solution between gels was drained by a vacuum pressure of 5 psi for 30 seconds. Thereafter, the weight was measured to calculate AUL by the same method as in the above measurement of absorbency under load, and the calculated AUL was referred to as "5-min gel-AU L".

(4) Gel Bed Permeability (GBP)

Gel bed permeability (GBP) was measured for each polymer. A method of measuring GBP is described in U.S. Pat. No. 7,179,851.

Specifically, the superabsorbent polymer according to the present invention exhibits particular properties or characteristics when free swell gel bed permeability (GBP) and gel bed permeability under load (0.3 GBP) were measured. The gel bed permeability test (GBP) is a measurement of the permeability, expressed as Darcy, of a swollen bed of superabsorbent material (e.g., separate from the absorbent structure) under a confining pressure after what is commonly referred to as "free swell" conditions. The term "free swell" means that the superabsorbent material is allowed to swell without a swell restraining load upon absorbing a test solution. Gel bed permeability under load (0.3 GBP) means a permeability of a swollen bed of gel particles (e.g., superabsorbent polymer of the present invention) after the superabsorbent material is restrained by a confining pressure of about 0.3 psi.

—Test of Free Swell Gel Bed Permeability (GBP)

First, the free swell gel bed permeability (GBP) test determines the permeability of a swollen bed of gel particles (e.g., absorbent materials after surface treatment or absorbent materials before surface treatment) under what is commonly referred to as "free swell" conditions. The term "free swell" means that the gel particles are allowed to swell without a restraining load upon absorbing a test solution. A suitable apparatus for conducting a permeability test is shown in FIGS. 3 and 4 and indicated generally by 28 of FIG. 3. The test apparatus 28 includes a sample container (generally indicated by 30) and a piston (generally indicated by 36). The piston 36 includes a cylindrical LEXAN® shaft 38 having a concentric cylindrical hole 40 bored down the longitudinal axis of the shaft. Both ends of the shaft 38 are machined to provide upper and lower ends (indicated by 42 and 46, respectively). A weight (indicated by 48) rests on one end 42 and has a cylindrical hole 48a bored through at least a portion of its center.

A circular piston head 50 is positioned on the other end 46 and is provided with a concentric inner ring of seven holes 60 (each having a diameter of about 0.95 cm), and a concentric outer ring of fourteen holes 54 (each having a diameter of about 0.95 cm). The holes 54, 60 are bored from the top to the bottom of the piston head 50. The piston head 50 also has a cylindrical hole 62 bored in the center thereof to receive end 46 of the shaft 38. The bottom of the piston head 50 may also be covered with a biaxially stretched 400 mesh stainless steel screen 64.

The sample container 30 includes a cylinder 34 and a 400 mesh stainless steel cloth screen 66 that is biaxially stretched to tautness and attached to the lower end of the cylinder. A superabsorbent polymer sample (indicated by 68 in FIG. 3) is supported on the screen 66 within the cylinder 34 during testing.

The cylinder 34 may be bored from a transparent LEXAN rod of equivalent material, or it may be cut from a LEXAN tubing or equivalent material, and has an inner diameter of about 6 cm (e.g., a cross sectional area of about 28.27 cm²), a wall thickness of about 0.5 cm and a height of about 10 cm. Drainage holes (not shown) are formed in the sidewall of the cylinder 34 at a height of about 7.8 cm above the screen 66 to allow liquid to drain from the cylinder, thereby maintaining a fluid level in the sample container at about 7.8 cm above screen 66. The piston head 50 is machined from a LEXAN rod or equivalent material and has a height of about 16 mm and a diameter sized such that it fits within the cylinder 34 with minimum wall clearance but still slides freely. The shaft 38 is machined from a LEXAN rod or equivalent material and has an outer diameter of about 2.22 cm and an inner diameter of about 0.64 cm.

The shaft upper end 42 is about 2.54 cm long and about 1.58 cm in diameter, forming an annular shoulder 47 to support the weight 48. The annular weight 48 has an inner diameter of about 1.59 cm so that it slips onto the upper end 42 of the shaft 38 and rests on the annular shoulder 47 formed thereon. The annular weight 48 may be made from stainless steel or from other suitable materials resistant to corrosion in the presence of the test solution, which is 0.9% by weight of sodium chloride solutions in distilled water. The combined weight of the piston 36 and annular weight 48 equals about 596 g, which corresponds to a pressure applied to the absorbent structure sample 68 of about 0.3 psi, or about 20.7 g/cm², over a sample area of about 28.27 cm².

When the test solution flows through the test apparatus during testing as described below, the sample container 30 generally rests on a 16 mesh rigid stainless steel support screen (not shown). Alternatively, the sample container 30 may rest on a support ring (not shown) diametrically sized substantially the same as the cylinder 34 so that the support ring does not restrict flow from the bottom of the container.

To conduct the gel bed permeability test under "free swell" conditions, the piston 36, with the weight 48 seated thereon, is placed in an empty sample container 30 and the height from the bottom of the weight 48 to the top of the cylinder 34 is measured using a calliper of suitable gauge accurate to 0.01 mm. It is important to measure the height of each sample container 30 empty and to keep track of which piston 36 and weight 48 is used when using a multiple test apparatus. The same piston 36 and weight 48 should be used for measurement when the superabsorbent polymer sample 68 is water swollen following saturation.

The sample to be tested is prepared from superabsorbent material particles which are prescreened through a US standard 30 mesh screen and retained on a US standard 50 mesh screen. As a result, the test sample includes particles sized in the range of about 300 to about 600 µm. The particles may be prescreened by hand or automatically. About 2.0 g of the sample is placed in the sample container 30, and the container, without the piston 36 and weight 48 therein, is then submerged in the test solution for a time period of about 60 minutes to saturate the sample and allow the sample to swell free of any restraining load.

At the end of this period, the piston 36 and the weight 48 are placed on the saturated sample 68 in the sample container 30 and then the sample container 30, piston 36, weight 48, and sample 68 are removed from the solution. The thickness of the saturated sample 68 is determined by again measuring the height from the bottom of the weight 48 to the top of the cylinder 34, using the same calliper or gauge used previously (provided that the zero point is unchanged from the initial height measurement). The height measurement obtained from measuring the empty sample container 30, piston 36, and weight 48 is subtracted from the height measurement obtained after saturating the sample 48. The resulting value is the thickness or height "H" of the swollen sample.

The permeability measurement is initialed by delivering a flow of the test solution into the sample container 30 with the saturated sample 68, piston 36, and weight 48 inside. The flow rate of the test solution into the container is adjusted to maintain a fluid height of about 7.8 cm above the bottom of the sample container. The quantity of solution passing through the sample 68 versus time is measured gravimetrically. Data points are collected every second for at least 20 seconds once the fluid level has been stabilized to and maintained at about 7.8 cm in height. The flow rate Q through the swollen sample 68 is determined in units of g/s by a linear least-square fit of fluid passing through the sample 68 (g) versus time (sec).

Permeability (Darcy) is obtained by the following Equation:

$$K=[Q\times H\times Mu]/[A\times Rho\times P] \qquad \text{[Mathematical Equation 3]}$$

where K is a permeability (cm²), Q is a flow rate (g/rate), H is a height of the sample (cm), Mu is a liquid viscosity (poise) (approximately 1 cps for the test solution used in the test), A is a cross-sectional area for liquid flow (cm²), Rho is a liquid density (g/cm³) (for the test solution used in this test) and P is a hydrostatic pressure (dynes/cm²) (normally approximately 3.923 dynes/cm²). The hydrostatic pressure is calculated from the following Equation:

$$P=Rho\times g\times h \qquad \text{[Mathematical Equation 4]}$$

wherein Rho is a liquid density (g/cm²), g is gravitational acceleration, nominally 981 cm/sec², and h is a fluid height (e.g., 7.8 cm for the permeability test described herein).

—Test of Gel Bed Permeability Under Load

The gel bed permeability under load test (otherwise referred to herein as GBP at 0.3 psi) determines the permeability of a swollen bed of gel particles (e.g., absorbent materials after surface treatment or absorbent materials before surface treatment), under conditions that are commonly referred to as being "under load" conditions. The term "under load" means that swelling of the particles is restrained by a load generally consistent with normal usage loads applied to the particles (e.g., sitting, walking, twisting/etc.) by the wearer.

More particularly, the gel bed permeability under load test is substantially the same as the free swell gel bed permeability previously described with the following exception. After about 2.0 g of the sample is placed in the sample container 30 and spread out evenly on the bottom of the sample container, the piston 36 and weight 48 are placed on the sample within the sample container prior to the sample container (with the piston and weight therein) being submerged in the test solution (0.9% by weight of NaCl saline) for a time period of about 60 minutes. As a result, a 0.3 psi restraining load is applied to the sample as the sample becomes saturated and swells.

Results of the measurement are given in the following Table 1.

TABLE 1

|  | 5-min gel-AUL(g/g) | CRC(g/g) | AUL(g/g) | GBP(Darcy) | A:B[1] |
|---|---|---|---|---|---|
| Example 1 | 18.3 | 31.0 | 19.4 | 66 | 4.8:5.2 |
| Example 2 | 18.7 | 30.7 | 20.1 | 62 | 4.3:5.7 |
| Example 3 | 19.4 | 30.8 | 19.7 | 73 | 5.8:4.2 |
| Example 4 | 19.3 | 31.2 | 19.6 | 78 | 6.5:3.5 |

TABLE 1-continued

| | 5-min gel-AUL(g/g) | CRC(g/g) | AUL(g/g) | GBP(Darcy) | A:B[1) |
|---|---|---|---|---|---|
| Comparative Example 1 | 16.7 | 30.4 | 18.3 | 54 | 1.7:8.3 |
| Comparative Example 2 | 17.5 | 30.1 | 17.9 | 35 | 2.8:7.2 |

[1)]A: a total pore area ratio of micropores having a diameter of 5 μm to 100 μm, B: a total pore area ratio of macropores having a diameter of 100 μm to 400 μm.

As shown in Table 1, the superabsorbent polymers of Examples according to the present invention exhibits a high absorption rate under load while maintaining centrifuge retention capacity similar to that of the polymers of Comparative Examples. Therefore, the superabsorbent polymers according to the present invention may be used to more easily produce diapers, to which an ultra-thin technology is applied.

The invention claimed is:

1. A porous superabsorbent polymer comprising
a crosslinked polymer resulting from polymerization and internal crosslinking of a monomer composition comprising acrylic acid-based monomers having acidic groups which are at least partially neutralized, a low-temperature foaming agent, and a high-temperature foaming agent, and
a surface crosslinking layer formed on the surface of the crosslinked polymer,
wherein the superabsorbent polymer has centrifuge retention capacity (CRC) as 29.5 g/g or more, absorbency under load (AUL) as 18 g/g or more, gel bed permeability (GBP) as 60 Darcy or more, and 5-min gel-AUL as 18.0 g/g or more,
wherein a ratio (A:B) of a total pore area (A) of micropores having a diameter of 5 μm to 100 μm and a total pore area (B) of macropores having a diameter of 100 μm to 400 μm in the superabsorbent polymer is 3:7 to 9:1, and the micropores and the micropores have different diameters, and
a weight ratio of the low-temperature foaming agent and the high-temperature foaming agent is 50:1 to 2:1.

2. The porous superabsorbent polymer of claim 1, wherein the ratio (A:B) is 4:6 to 8:2.

3. The porous superabsorbent polymer of claim 1, wherein the low-temperature foaming agent is sodium bicarbonate, sodium carbonate, potassium bicarbonate, potassium carbonate, calcium bicarbonate, calcium carbonate, magnesium bicarbonate, or magnesium carbonate.

4. The porous superabsorbent polymer of claim 1, wherein the high-temperature foaming agent is azodicarbonamide (ADCA), dinitroso pentamethylene tetramine (DPT), p,p'-oxybisbenzenesulfonylhydrazide (OBSH), p-toluenesulfonyl hydrazide (TSH), or sugar ester.

5. The porous superabsorbent polymer of claim 1, wherein the acrylic acid-based monomer is represented by the following Chemical Formula 1:

$R_1-COOM^1$     [Chemical Formula 1]

wherein,
$R_1$ is an alkyl group containing an unsaturated bond and having 2 to 5 carbon atoms, and
$M^1$ is a hydrogen atom, a monovalent or divalent metal, an ammonium group, or an organic amine salt.

6. The porous superabsorbent polymer of claim 1, wherein the acrylic acid-based monomer comprises one or more selected from the group consisting of acrylic acid, methacrylic acid, and a monovalent metal salt, a divalent metal salt, an ammonium salt, and an organic amine salt thereof.

7. The porous superabsorbent polymer of claim 1, wherein the crosslinked polymer is internally crosslinked by one or more first crosslinking agents selected from the group consisting of N,N'-methylenebisacrylamide, trimethylolpropane tri(meth)acrylate, ethylene glycol di(meth)acrylate, polyethylene glycol (meth)acrylate, propylene glycol di(meth)acrylate, polypropylene glycol (meth)acrylate, butanediol di(meth)acrylate, butylene glycol di(meth)acrylate, diethylene glycol di(meth)acrylate, hexanediol di(meth)acrylate, triethylene glycol di(meth)acrylate, tripropylene glycol di(meth)acrylate, tetraethylene glycol di(meth)acrylate, dipentaerythritol pentacrylate, glycerin tri(meth)acrylate, pentaerythritol tetraacrylate, triarylamine, ethylene glycol diglycidyl ether, propylene glycol, glycerin, and ethylene carbonate.

8. The porous superabsorbent polymer of claim 1, wherein the superabsorbent polymer is a particulate polymer having a particle diameter of 150 to 850 μm.

* * * * *